US00PP13931P29

(12) United States Plant Patent
Lyrene

(10) Patent No.: US PP13,931 P2
(45) Date of Patent: Jul. 1, 2003

(54) BLUEBERRY PLANT CALLED 'SOUTHERN BELLE'

(75) Inventor: Paul M. Lyrene, Gainesville, FL (US)

(73) Assignee: Florida Foundation Seed Producers, Inc., Greenwood, FL (US)

( * ) Notice: Subject to any disclaimer, the term of this patent is extended or adjusted under 35 U.S.C. 154(b) by 4 days.

(21) Appl. No.: 10/038,446

(22) Filed: Jan. 7, 2002

(51) Int. Cl.[7] ..... A01H 5/00
(52) U.S. Cl. ..... Plt./157
(58) Field of Search ..... Plt./157, 156

*Primary Examiner*—Bruce R. Campell
*Assistant Examiner*—June Hwu

(57) ABSTRACT

'Southern Belle' is a new southern highbush blueberry variety that originated as a seedling selected from the University of Florida recurrent selection program, in which genes from *Vaccinium corymbosum* and *V. darrowi* were being combined and selected to obtain varieties that are adapted to mild-winter regions and produce large, high-quality berries early in the harvest season. 'Southern Belle' has been tested in clonal plots in south Georgia and north Florida since 1984. 'Southern Belle' produces a vigorous, low-chill bush that sprouts abundantly from the base, and produces a heavy crop of fruit on stout, upright stems that can reach 4 to 5 m tall if not pruned. The berries, which ripen in late April and early May in north Florida, are large and have a very small, dry picking scar, as well as good firmness and a mild, subacid flavor. The berry picks free of stems and adhering dried corollas and has excellent post-harvest life if stored at 32° F. The plant propagates readily from softwood cuttings. It is only moderately resistant to stem blight and Phytophthora root rot, and should be planted on good blueberry ground with irrigation and annual pruning to maintain plant health and vigor.

4 Drawing Sheets

Latin name of genus and species of the plant claimed: Corresponds approximately to *Vaccinium corymbosum* L. The clone, however, is a hybrid, and in its ancestry are also some genes from *Vaccinium darrowi* Camp.

Variety denomination: Southern Belle.

BACKGROUND OF THE INVENTION

'Southern Belle' is a low-chill southern highbush blueberry clone intended for production of blueberry fruit that can be harvested early in the season when the clone is grown in areas with mild winters. Although the fruit can be frozen or otherwise processed, it is anticipated that most of the production will be harvested for fresh-market shipments early in the harvest season. 'Southern Belle' is the product of an interspecific hybridization program, and thus does not correspond to any species. The parent species used to breed 'Southern Belle' were *Vaccinium corymbosum* L. and *V. darrowi* Camp. 'Southern Belle' is not a simple hybrid between these species, but rather is the product of many generations of recurrent selection in which genes of these two species were repeatedly recombined.

'Southern Belle' is a vegetatively propagated clone derived from a seedlings planted at the Horticultural Unit of the University of Florida in Gainesville, Fla. in about 1980. The seedling was grown from a seed produced by hand-pollination of potted blueberry plants in a greenhouse in Gainesville. Although the exact pedigree of 'Southern Belle' is unknown, the seedling is the result of 5 to 8 generations of recurrent selection in which the best features of northern highbush cultivars from Michigan and New Jersey (all unpatented) were being combined with the heat tolerance and low chilling requirement of the Florida native blueberry species *Vaccinium darrowi*. The seedling was selected from a population of approximately 10,000 that were being tested in a field nursery. It was chosen because of its large fruit size, high firmness, small, dry picking scar, and good flavor.

Softwood cuttings from the seedling were rooted and were used to establish a clonal plot near Homerville, Ga. in 1984. Because the clonal plot had high yields, large berry size, and high fruit quality compared to other selections being tested at the location, 'Southern Belle' was repeatedly propagated by softwood cuttings until more than 10,000 plants had been planted in the field by 1996. Asexual propagation by softwood cuttings has repeatedly produced plants uniform in characteristics and identical to the original seedling in all distinguishing characteristics. 'Southern Belle' is genetically stable when propagated by softwood cuttings.

SUMMARY OF THE INVENTION

'Southern Belle' has the following novel combination of characteristics that set it apart from other blueberry varieties:

1. It flowers and produces new leaves readily in the spring when grown in areas where the mean January temperature is as high as 55 degrees F.

2. It produces a large, firm berry with a small dry scar and a sweet, sub-acid flavor. Mean berry weight on healthy, well-pruned plants averages 2.3 g per berry.

3. It produces high yields of berries borne on stout stems produced from a thicket of vigorous canes sprouting from the crown of the plant.

4. It roots readily from softwood cuttings.

5. When grown in north-central Florida (mean January temperature 56° F.), the average date of 50% open flower is March 1 and the average date of 50% ripe fruit is April 28.

6. It has excellent packinghouse qualities—when hand-harvested, the berries are free of stems, skin tears, or adhering dried corollas. The storage life as a fresh berry at 32° F. is unusually long for a southern highbush cultivar.

7. The berry color is medium to light blue.

8. The clone is tetraploid, with a somatic chromosome number 48.

BRIEF DESCRIPTION OF THE DRAWINGS

The accuracy of the colors in these drawings is limited by the photographic techniques used. Where colors in the drawings differ from the Pantone color designations in the verbal descriptions, the Pantone color designations are the more accurate.

The first drawing shows a 5-year-old plant of 'Southern Belle' approximately 2 m tall in early May in a field near Gainesville, Fla. The upright growth habit, dense canopy, and tendency to make numerous sprouts from the base can be seen.

The second drawing shows opened and unopened flowers of 'Southern Belle'.

The third drawing shows in close view the leaves and one cluster of ripening fruit of 'Southern Belle'.

The fourth drawing shows in close view a stem of 'Southern Belle' with several clusters of ripening fruit. The poorly developed calyx lobes on the mature berries are visible, along with the rather flat shape of the berry.

BOTANICAL DESCRIPTION OF THE PLANT

'Southern Belle' is a complex interspecific hybrid derived from a program of recurrent crossing and selection following hybridization of the species *Vaccinium corymbosum* and *V. darrowi*. The exact parents are unknown, but were unpatented selections from the University of Florida recurrent selection program. 'Southern Belle' is a clone which is commercially important because it can produce high yields of high-quality berries during late April and early May when grown in northern Florida and southeastern Georgia. Descriptions of various aspects of 'Southern Belle' are presented below.

Bush: The following measurements were taken from 5-year-old plants planted in a bed of pine bark at 1 m×1.5 m spacing in Gainesville, Fla. The plants had been fertilized and irrigated as recommended for commercial producers.

*Plant height.*—2.0 m.

*Canopy diameter at widest point.*—1.2 m.

*Plant vigor.*—High; about equal to 'Sharpblue' (unpatented).

*Growth habit.*—Upright. Numerous canes rising from a narrow crown.

*Flower bud density (number) along reproductive twigs in January.*—High; Higher than for 'Sharpblue' (unpatented).

*Twiggines.*—Low.

*Tendency toward evergreenness during winter in Gainesville.*—Medium to low. Less than for 'Sharpblue' (unpatented).

Trunk: Suckering tendency. High. Average of 15 strong canes rising from the crown of 5-year-old plants grown in pine bark. Higher than for 'Sharpblue'.

*Surface texture of current-year shoots observed August 1.*—Smooth.

*Surface texture of 1-year-old shoots observed August 1.*—Smooth.

*Surface texture of 3-year-old and older canes near base.*—Rough.

*Color of 6-months-old strong new growth viewed August 1.*—"Tarragon", Pantone 15-0326.

*Color of 1-year-old smooth canes observed August 1.*—"Hay", Pantone 12-0418.

*Color of 3-year-old rough canes viewed August 1.*—"Oyster white", Pantone 13-1007.

Twigs:

*Color of current-season twigs observed August 1.*—"Hay", Pantone 12-0418.

*Surface texture of twigs.*—Smooth.

*Mean internode length for strong new upright shoots measured 1 August.*—1.15 cm.

Leaves:

*Petiole length.*—5 mm.

*Leaf length measured on fully-expanded leaves on vigorous flushes.*—Leaf size is quite variable. Leaf measurements were based on the largest 25% of the leaves. Leaf lengths include the petiole and leaf blade. Mean. 7.1 cm.

*Leaf width.*—3.5 cm.

*Leaf shape.*—Ovate with an acute apex. Leaf apex terminates in a small dew tip, about 0.3 mm long.

*Leaf margin.*—Entire except for a few marginal leaf glands along the margins of the petioliar one-third of the leaf, which are visible under 30× magnification.

*Color of upper surface of leaves.*—"Periodot", Pantone 17-0336.

*Color of lower surface of leaves.*—"Tarragon", Pantone 15-0326.

*Pubescence on upper surface of leaves.*—Numerous short, white hairs on midrib of upper surface visible under 30× magnification.

*Pubescence on lower surface of leaves.*—Little or none.

Flowers:

*Flower arrangement.*—Flowers arranged alternately along a short, leafless, deciduous branch.

*Fragrance.*—Little or none.

*Pedicel length at the time of anthesis.*—Mean 3.6 mm; range 2–6 mm.

*Peduncle length at the time of anthesis.*—Mean 7 mm; range 4–12 mm.

*Petals.*—Fused into a corolla tube with 5 lobes.

*Pollen staining.*—Approximately 97% of the pollen grains stain in acetocarmine dye indicating that a high percentage of the pollen grains are well-formed, starch filled, and potentially viable.

*Pollen abundance.*—Dried flowers shed pollen abundantly.

*Pollen color.*—Dried pollen is "Yolk yellow", Pantone 14-0846.

*Flower type.*—Perfect, ovary inferior, petals fused into a corolla tube, the 10 stamens inserted at the base of the corolla tube.

*Flower length, pedicel attachment point to corolla tip.*—Mean 10.8 mm.

*Style length, top of ovary to stigma tip.*—Mean 8.2 mm.

*Calyx diameter at anthesis, tip of lobe to tip of opposite lobe.*—Mean 6.3 mm.

*Diameter of corolla tube at widest point.*—Mean 7.5 mm.

*Corolla aperture diameter.*—Mean 3.2 mm.

*Corolla surface texture.*—Smooth.

*Flower shape.*—Cylindrical.

*Corolla color at anthesis.*—"Turtledove", Pantone 12-5202 (a type of white).

*Calyx color at anthesis.*—"Leaf Green", Pantone 15-0332.

*Flowering period.*—Mean date of 50% open flower in Gainesville, Fla. March 1.

*Flower cluster* (*tight, medium, or open*).—Medium.

*Number of flowers per cluster.*—Mean 5.8.

*Self fruitfulness.*—Low. Requires cross-pollination for high yields. From 99 flowers manually self-pollinated in a greenhouse in March 2000, only 7 small berries formed.

*Location of tip of style relative to lip of corolla.*—Tip of style 1–2 mm too short to reach the tip of the corolla.

Berry:

*Mean date of 50% berry ripening in Gainesville, Fla.*—April 28.

*Diameter of calyx aperture on mature berry.*—5 mm.

*Calyx lobes on mature berry.*—Size and shape. Calyx aperture alightly recessed into berry; calyx lobes irregular in shape and not well developed.

*Berry cluster* (*tight, medium, or open*).—Medium.

*Pedicel length of ripe berry.*—Mean 6.7 mm.

*Peduncle length of ripe berries.*—Mean 9.8 mm.

*Mean number of ripe berries per cluster.*—4.8.

*Mean berry weight on well-pruned plants.*—2.3 g.

*Mean berry height.*—14 mm.

*Mean berry width.*—17 mm.

*Berry color* (*ripe*) *on plant.*—"Dapple gray" Pantone 16-3907.

*Berry color after harvest and modest handling.*—"Frost gray", Pantone 17-0000.

*Berry skin color after polishing.*—"Shale", Pantone 19-3903.

*Internal flesh color of ripe berry.*—"Silver fern", Pantone 15-0719.

*Berry surface wax.*—Medium thick and above-average in persistence when berry is handled.

*Berry pedicel scar.*—Very small and dry.

*Berry firmness.*—High.

*Berry flavor.*—Mild; sugar and acidity somewhat less than for 'Sharpblue', (unpatented).

*Berry texture.*—Small seeds and not "gritty".

*Color of dried seeds.*—"Brown sugar", Pantone 17-1134.

*Weight of well-developed, dried seeds.*—0.61 mg per seed.

*Length of well-developed seed.*—2.0 mm.

*Width of well-developed seed.*—1.1 mm.

Physiological characteristics:

*Cold hardiness.*—Flowers, berries, and tender growth hardy to 28° F. Well-hardened plants and flower buds in full winter dormancy hardy to 0° F.

*Chilling requirement.*—400 hours per winter below 45° F.

*Productivity.*—Four-year-old plantings in pine bark with overhead irigation in north-central Florida yield about 8,000 kg/ha at a plant density of 4,000 plants per hectare.

*Ease of propagation.*—Propagates readily from softwood cuttings.

Diseases, insects, and mites:

*Phytophtora root rot.*—Medium susceptible; more susceptible than 'Sharpblue' (unpatented).

*Stem blight* (*Botryosphaeria dothidia*).—Medium susceptible; more susceptible than 'Sharpblue' (unpatented).

*Cane canker* (*Botryosphaeria corticis*).—Resistant to common races.

*Fungal and bacterial leaf spots.*—Above average resistance.

*Blueberry bud mites.*—Above average resistance.

*Overall survival in the field.*—Somewhat below average for southern highbush blueberry. Requires well-drained soil for good growth and survival.

I claim:

1. A new and distinct highbush blueberry plant, substantially as illustrated and described, characterized by its low chilling requirement, large, firm berry, small, dry picking scar, and high yield potential.

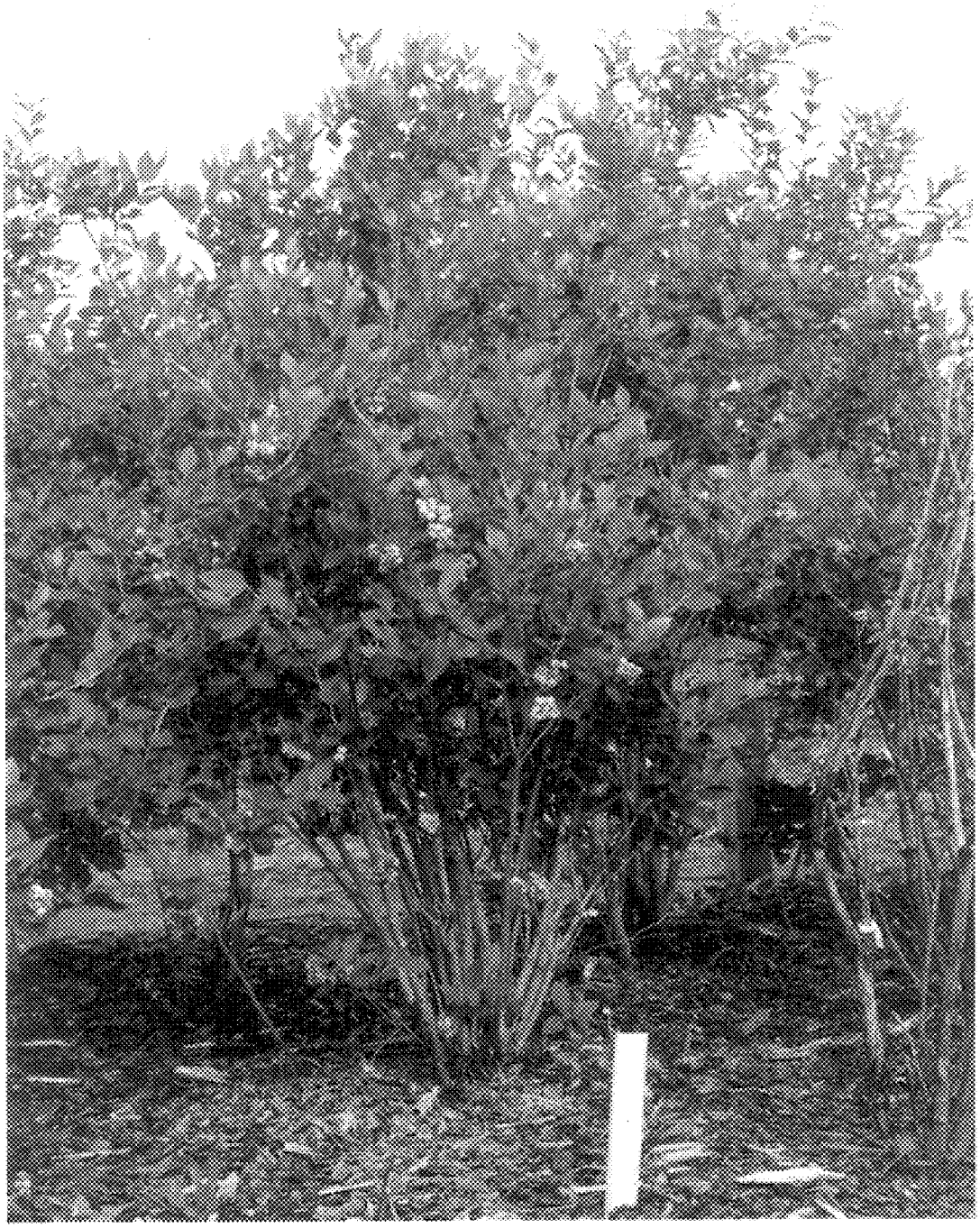

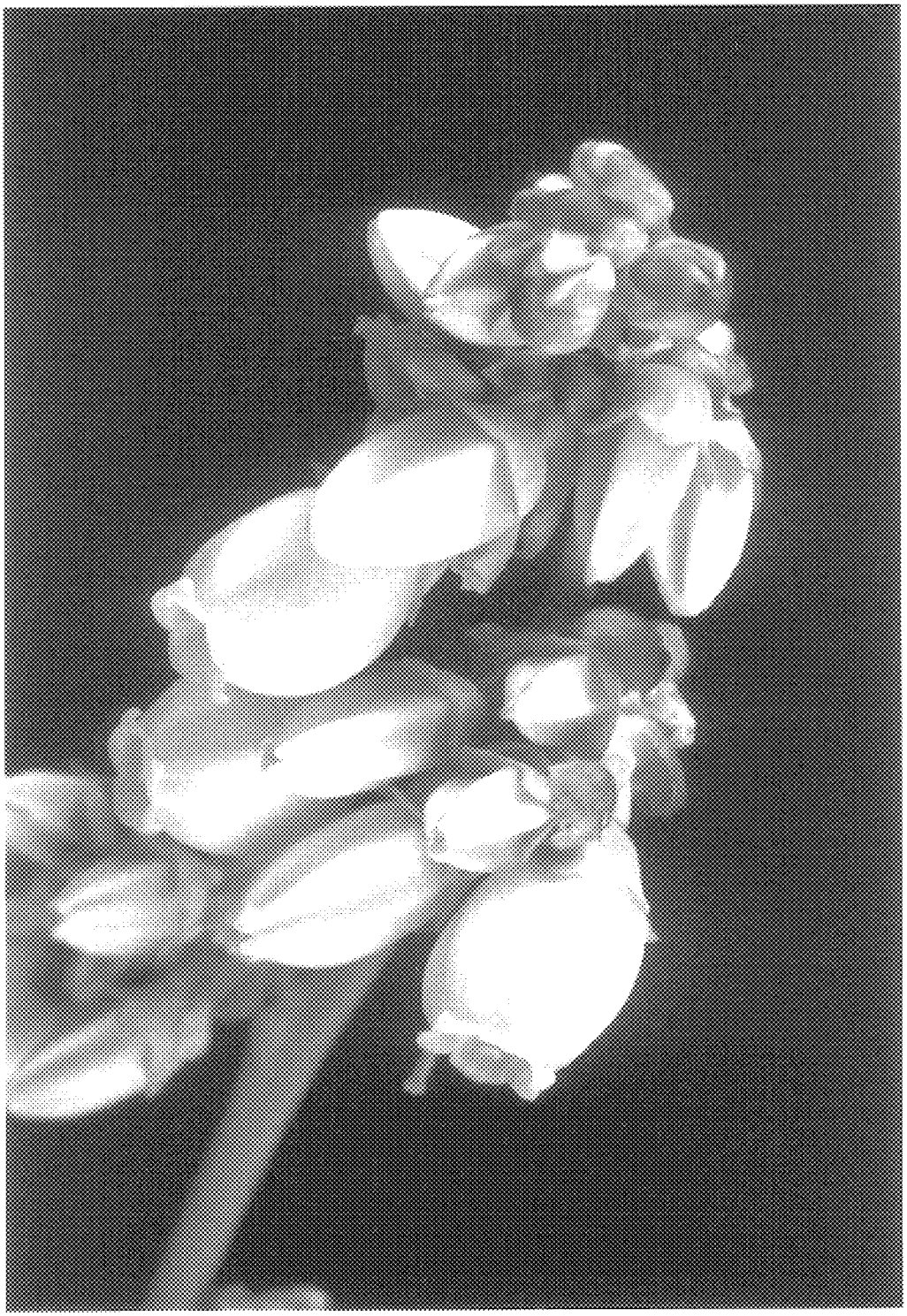

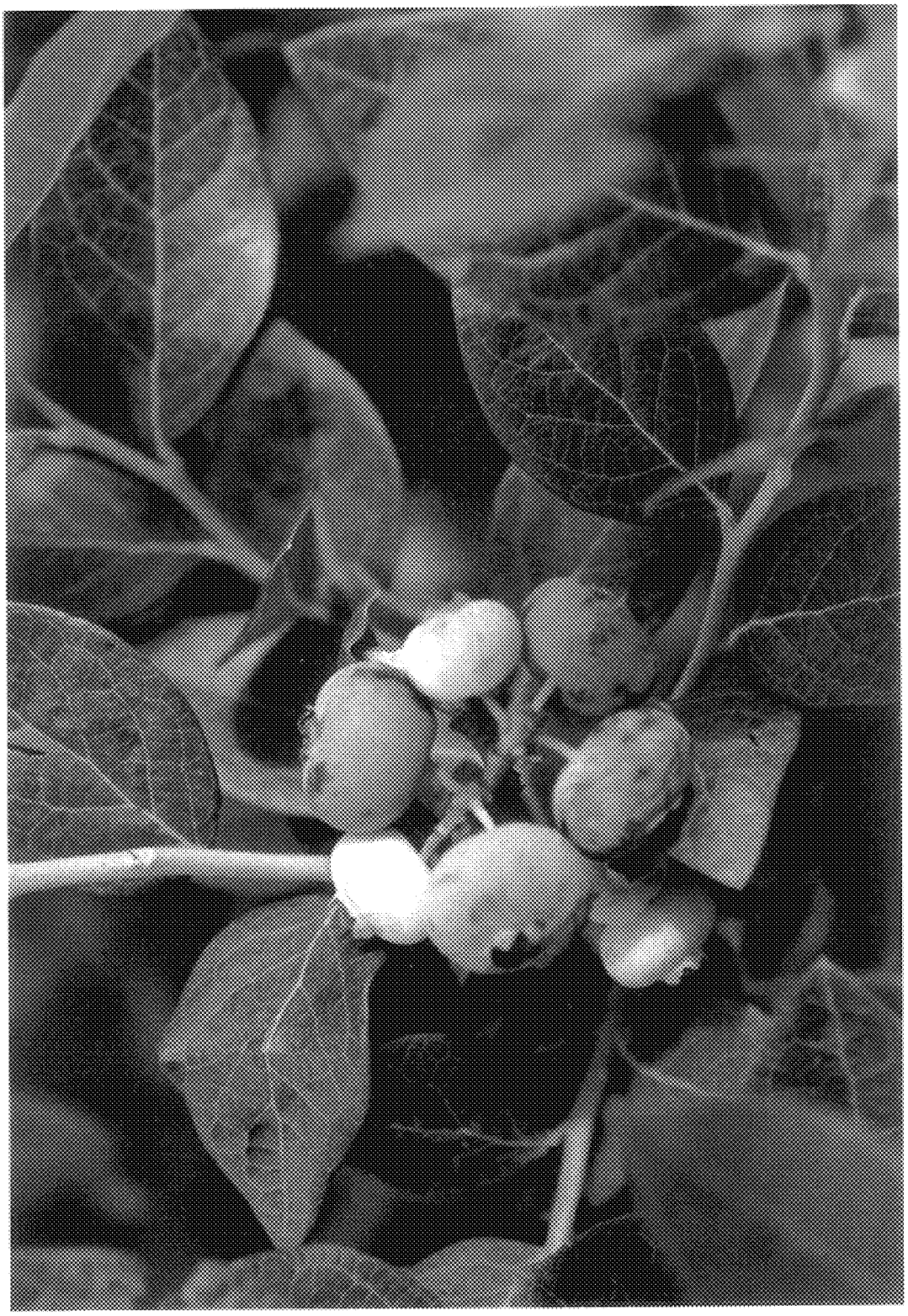

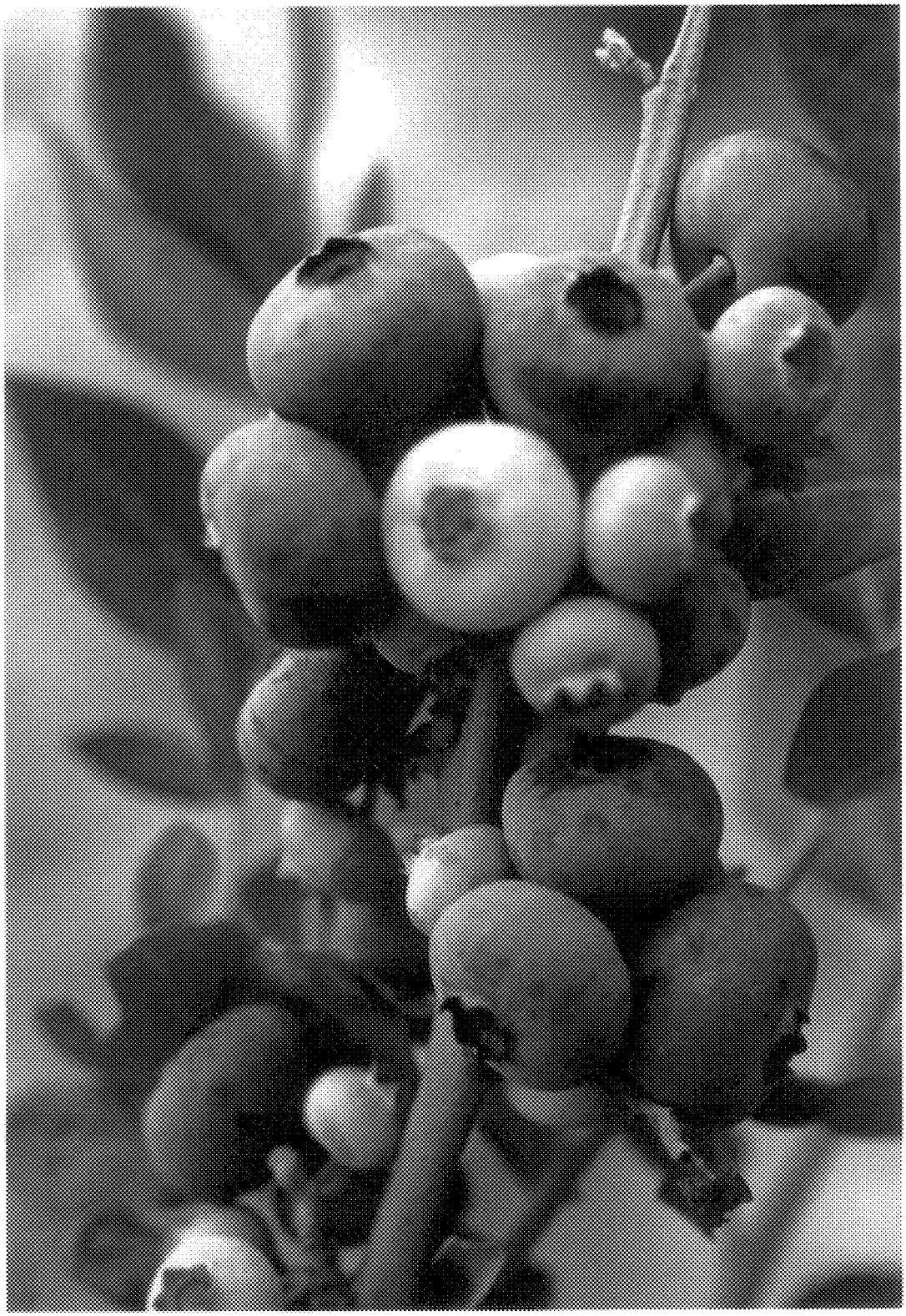

* * * * *